United States Patent
McMahon et al.

(10) Patent No.: US 10,143,386 B2
(45) Date of Patent: *Dec. 4, 2018

(54) RANGE GATED RADIO FREQUENCY PHYSIOLOGY SENSOR

(71) Applicant: ResMed Sensor Technologies Limited, Dublin (IE)

(72) Inventors: Stephen McMahon, Dublin (IE); Michael Wren, Dublin (IE); Spencer Terry Wood, Shanklin (GB); Kieran Conway, Clane (IE); Conor Heneghan, San Diego, CA (US)

(73) Assignee: ResMed Sensor Technologies Limited (AU)

( * ) Notice: Subject to any disclaimer, the term of this patent is extended or adjusted under 35 U.S.C. 154(b) by 143 days.

This patent is subject to a terminal disclaimer.

(21) Appl. No.: 14/415,677

(22) PCT Filed: Jul. 19, 2013

(86) PCT No.: PCT/US2013/051250
§ 371 (c)(1),
(2) Date: Jan. 19, 2015

(87) PCT Pub. No.: WO2014/015238
PCT Pub. Date: Jan. 23, 2014

(65) Prior Publication Data
US 2015/0216424 A1    Aug. 6, 2015

Related U.S. Application Data

(60) Provisional application No. 61/673,774, filed on Jul. 20, 2012.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0507* (2013.01); *A61B 5/11* (2013.01);
(Continued)

(58) Field of Classification Search
CPC ................................. A61N 1/025; A61B 5/05
(Continued)

(56) References Cited

U.S. PATENT DOCUMENTS 4,197,537 A    4/1980   Follen et al.
4,238,796 A    12/1980  Mawhinney
(Continued)

FOREIGN PATENT DOCUMENTS

CN    101489478 A    7/2009
CN    102404003 A    4/2012
(Continued)

OTHER PUBLICATIONS

Dellsperger. Device Evaluation for Current-Mode Class-D RF Power Amplifiers. Diploma thesis written at the University of California, Santa Barbara. Aug. 8, 2003.
(Continued)

*Primary Examiner* — Carl H Layno
*Assistant Examiner* — Jon Eric C Morales
(74) *Attorney, Agent, or Firm* — Botos Churchill IP Law LLP

(57) ABSTRACT

A sensor for physiology sensing may be configured to generate oscillation signals for emitting radio frequency pulses for range gated sensing. The sensor 402 may include a radio frequency transmitter configured to emit the pulses and a receiver configured to receive reflected ones of the emitted radio frequency pulses. The received pulses may be processed to detect physiology characteristics such as motion, sleep, respiration and/or heartbeat. In some embodiments, the sensor may employ a circuit including a pulse (Continued)

generator configured to generate signal pulses. The circuit may also include a dielectric resonator oscillator configured to generate a radio frequency oscillating signal. A switched oscillation circuit may be coupled to the pulse generator and the dielectric resonator oscillator. The switched circuit may be configured to generate a pulsed radio frequency oscillating signal for emitting the radio frequency pulses.

32 Claims, 10 Drawing Sheets

(51) Int. Cl.
*A61B 5/05* (2006.01)
*G01S 7/282* (2006.01)
*G01S 13/18* (2006.01)
*G01S 13/56* (2006.01)
*H03B 5/18* (2006.01)
*A61B 5/08* (2006.01)
*A61B 5/11* (2006.01)
*A61B 5/024* (2006.01)

(52) U.S. Cl.
CPC .......... *A61B 5/1126* (2013.01); *A61B 5/4836* (2013.01); *A61B 5/7225* (2013.01); *G01S 7/282* (2013.01); *G01S 13/18* (2013.01); *G01S 13/56* (2013.01); *H03B 5/187* (2013.01); *A61B 5/024* (2013.01); *A61B 5/0816* (2013.01); *A61B 5/1102* (2013.01); *A61B 5/4809* (2013.01)

(58) Field of Classification Search
USPC ...................................... 600/301; 607/32, 60
See application file for complete search history.

(56) References Cited

U.S. PATENT DOCUMENTS

| | | |
|---|---|---|
| 4,631,497 A | 12/1986 | Braun |
| 5,107,272 A | 4/1992 | Joynson et al. |
| 5,142,251 A | 8/1992 | Boomer |
| 5,309,453 A | 5/1994 | Treacy |
| 5,361,070 A | 11/1994 | McEwan |
| 5,623,233 A | 4/1997 | Higgins et al. |
| 5,682,164 A | 10/1997 | McEwan |
| 5,757,241 A | 5/1998 | Simonutti |
| 5,966,090 A | 10/1999 | McEwan |
| 5,986,600 A | 11/1999 | McEwan |
| 6,087,972 A | 7/2000 | Puglia et al. |
| 6,166,533 A | 12/2000 | Musha |
| 6,426,716 B1 | 7/2002 | McEwan |
| 6,535,766 B1 | 3/2003 | Thompson et al. |
| 7,608,808 B2 | 10/2009 | Kuramoto |
| 7,952,515 B2 | 5/2011 | McEwan |
| 8,138,844 B1 | 3/2012 | Simmons et al. |
| 9,333,034 B2 | 5/2016 | Hancock |
| 9,445,729 B2 * | 9/2016 | McMahon .......... A61B 5/4836 |
| 2001/0051766 A1 | 12/2001 | Gazdzinski |
| 2004/0249258 A1 | 12/2004 | Tupin et al. |
| 2005/0190101 A1 | 9/2005 | Hiramatsu et al. |
| 2005/0203348 A1 | 9/2005 | Shihadeh et al. |
| 2008/0045832 A1 | 2/2008 | McGrath |
| 2008/0211549 A1 | 9/2008 | Bolton et al. |
| 2008/0278369 A1 | 11/2008 | Milano |
| 2009/0203972 A1 | 8/2009 | Heneghan et al. |
| 2010/0214158 A1 | 8/2010 | McEwan |
| 2012/0063504 A1 | 3/2012 | Simmons |
| 2012/0071710 A1 | 3/2012 | Gazdzinski |
| 2013/0140649 A1 | 6/2013 | Rogers et al. |
| 2013/0225988 A1 | 8/2013 | Mahfouz |

FOREIGN PATENT DOCUMENTS

| | | | |
|---|---|---|---|
| JP | H02-146849 A | 6/1990 | |
| JP | H07-094946 A | 4/1995 | |
| JP | 2009-538720 A | 11/2009 | |
| WO | 2005115235 A1 | 12/2005 | |
| WO | 2006-048544 A1 | 5/2006 | |
| WO | 2006059367 A1 | 6/2006 | |
| WO | 2007-143535 A2 | 12/2007 | |
| WO | 2011-006199 A1 | 1/2011 | |

OTHER PUBLICATIONS

IEEE Microwave and Wireless Components Letters, vol. 15, No. 4, Apr. 2005, "A Novel High-Efficiency Linear Transmitter Using Injection-Locked Pulsed Oscillator.".
International Search Report and Written Opinion for Application No. PCT/US2013/051250 dated Oct. 9, 2013.
R. Adler, "A study of locking phenomena in oscillators", Proc. IRE, vol. 34, No. 6, pp. 351-357, Jun. 1946.
S. Terry-Wood, "Miniature YBCO/MgO planar superconducting filter, oscillator and delayline structures", PhD Thesis, Portsmouth University, UK, May 2005.
Chinese Office Action for Application No. 2013800387573 dated Nov. 21, 2016.
Japanese Office Action dated Jun. 30, 2017 and English translation of comments for JP Application No. 2015-523278.
EP Office Action dated Jul. 27, 2017 for EP Application No. 13 819 553.2.
NZ Examination Report dated Sep. 15, 2017 to NZ Application No. 702970.
El-Gabaly , "Pulsed RF Circuits for Ultra Wideband Communications and Radar Applications", Queen's University Kingston, Ontario, Canada, Aug. 2011.
Extended European Search Report issued in corresponding EP application No. 13819553.2 dated Feb. 25, 2016.

* cited by examiner

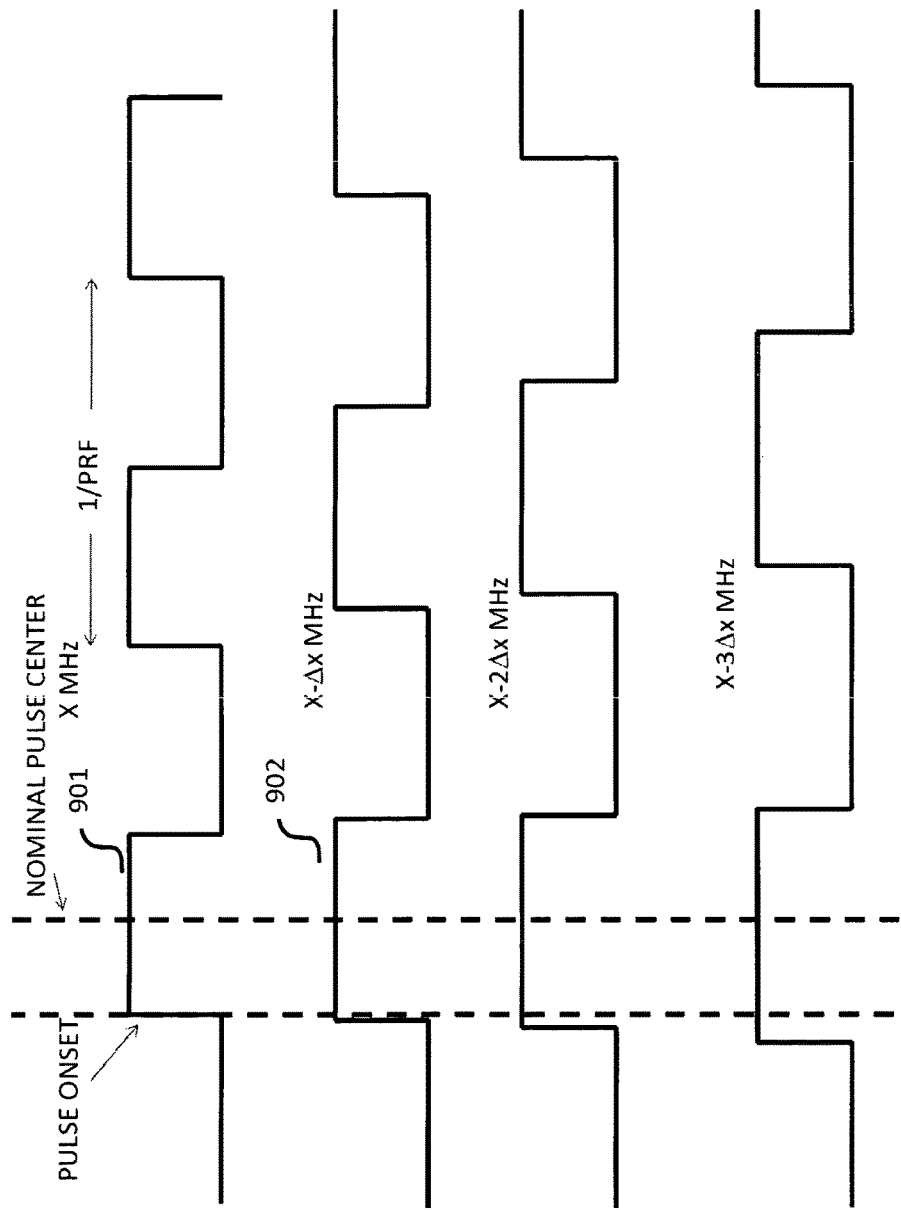

RANGE GATED RADIO FREQUENCY PHYSIOLOGY SENSOR

CROSS REFERENCE TO RELATED APPLICATIONS

This application claims the benefit of the filing date of U.S. Provisional Patent Application No. 61/673,774 filed Jul. 20, 2012, the disclosure of which is hereby incorporated herein by reference.

FIELD OF THE TECHNOLOGY

The present technology relates to circuits and sensors for detection of characteristics of moving objects and living subjects. More particularly, it relates to such sensors for generating range gated radio frequency pulses for motion sensing, with particular emphasis on measuring movements of people in order to determine physiological characteristics such as breathing, heart rate and movement.

BACKGROUND OF THE TECHNOLOGY

Continuous wave (CW) Doppler radar motion sensors emit a continuous wave radio frequency (RF) carrier and mix the transmitted RF with the return echoes to produce a difference frequency equal to the Doppler shift produced by a moving target. These sensors do not have a definite range limit (i.e., they can receive signals for both near and far objects, with the received signal being a function of radar cross section). This can lead to false triggers i.e., motion artefact interference. They may also have an undesirably high sensitivity at close range that leads to false triggering.

A pulse Doppler motion sensor is described in U.S. Pat. No. 4,197,537 to Follen et al. A short pulse is transmitted and its echo is self-mixed with the transmitted pulse. The pulse width defines the range-gated region. When the transmit pulse ends, mixing ends and target returns arriving after the end of the transmit pulse are not mixed and are thereby gated out.

A Differential pulse Doppler motion sensor disclosed in U.S. Pat. No. 5,966,090, "Differential Pulse Radar Motion Sensor," to McEwan, alternately transmits two pulse widths. It then subtracts the Doppler responses from each width to produce a range gated Doppler sensing region having a fairly constant response versus range.

Impulse radar, such as that described in U.S. Pat. No. 5,361,070, "Ultra-Wideband Radar Motion Sensor," to McEwan produces a very narrow sensing region that is related to the transmitted impulse width. A two-pulse Doppler radar motion sensor, as described in U.S. Pat. No. 5,682,164, "Pulse Homodyne Field Disturbance Sensor," to McEwan, transmits a first pulse and after a delay generates a second pulse that mixes with echoes from the first pulse. Thus a range gated sensing band is formed with defined minimum and maximum ranges. UWB radar motion sensors have the disadvantage of not having global RF regulatory acceptance as an intentional radiator. They also have difficulty sensing objects at medium ranges and in some embodiments can be prone to RF interference.

A modulated pulse Doppler sensor is described in U.S. Pat. No. 6,426,716 to McEwan. The range gated microwave motion sensor includes adjustable minimum and maximum detection ranges. The apparatus includes an RF oscillator with associated pulse generating and delay elements to produce the transmit and mixer pulses, a single transmit (TX)/receive (RX) antenna or a pair of separate TX and RX antennas, and an RF receiver, including a detector/mixer with associated filtering, amplifying and demodulating elements to produce a range gated Doppler signal from the mixer and echo pulses.

In U.S. Pat. No. 7,952,515, McEwan discloses a particular holographic radar. It adds a range gate to holographic radar to limit response to a specific downrange region. McEwan states that cleaner, more clutter-free radar holograms of an imaged surface can be obtained, particularly when penetrating materials to image interior image planes, or slices. The range-gating enables stacked hologram technology, where multiple imaged surfaces can be stacked in the downrange direction.

In U.S. Patent Application Publ. no. 2010/0214158, McEwan discloses an RF magnitude sampler for holographic radar. McEwan describes that the RF magnitude sampler can finely resolve interferometric patterns produced by narrowband holographic pulse radar.

There may be a need to improve sensors for pulse radio frequency sensing such as in the case of physiological characteristic detection.

SUMMARY OF THE TECHNOLOGY

One aspect of some embodiments of the present technology relates to a sensor for detecting physiology characteristics with radio frequency signals.

Another aspect of some embodiments of the technology relates to such a sensor with a circuit configured to generate pulsed radio frequency (RF) signals such as for range gating.

A still further aspect of some embodiments of the technology relates to a sensor with a circuit with improved oscillator design.

An additional aspect of some embodiments of the technology relates to such a sensor configured for improved RF oscillator frequency stability that also maintains fast switching characteristics desirable for range gating.

A further object of some embodiments of the technology is to provide an RF sensor that is amenable to radio frequency regulatory requirements as an intentional radiator.

Some embodiments of the present technology may include a radio frequency motion sensor. The sensor may include a radio frequency transmitter. The transmitter may be configured to emit radio frequency pulses. The sensor may also include a receiver configured to receive reflected ones of the emitted radio frequency pulses. The radio frequency transmitter may include a pulse generator configured to generate signal pulses; a dielectric resonator oscillator configured to generate a stable radio frequency oscillating signal; and a switched circuit coupled to the pulse generator and the dielectric oscillator. The switch circuit may be configured to generate a pulsed radio frequency oscillating signal whose dominant frequency is derived from the dielectric resonator oscillator.

In some cases, the dielectric resonator oscillator may include a dielectric resonator and a transistor.

Optionally, the switched circuit may be a switched wideband oscillator. A switched wideband oscillator is an oscillator circuit with a low-Q which has a specific input which allows the oscillator to be turned on or off. A switched wideband oscillator can be embodied using a Field Effect Transistor (FET) which includes a drain, a gate and a source configured such that the dielectric resonator oscillator may be coupled to the gate and drain of the transistor, and a pulse can be connected to the gate so that the oscillator can be turned on or off. Alternatively, the switched wideband oscillator can be based on a bipolar junction transistor (BJT) in which the switched circuit may include an emitter, base and collector such that the dielectric resonator may be coupled to the base and emitter of the transistor.

In some cases, the switched circuit may be a switchable radio-frequency amplifier. A switched amplifier is one in which there is an input and an output signal, together with a switch control signal. When the amplifier is turned on by a switch control signal, the output of the circuit will be an amplified version of the input. If the amplifier is turned off, there is no output. An embodiment of an amplifier may include a transistor having a drain, a gate and a source. The amplifier may be configured to amplify the radio frequency oscillating signal synchronously with the pulse signal to generate the pulsed radio frequency oscillating signal. The drain may be coupled to receive the signal pulses from the pulse generator. The gate may be coupled to receive the radio frequency oscillating signal from the dielectric resonator oscillator.

In some examples, the switched circuit may include a wideband oscillator. The wideband oscillator may be configured to injection lock with the dielectric resonator oscillator. Optionally, the wideband oscillator may include a transistor having a drain, a gate and a source. The wideband oscillator may also include a feedback network circuit coupled to the drain.

In some cases, the sensor may also include an attenuator and matching network circuit between an output of the dielectric resonator oscillator and an input of the switched circuit. The matching network circuit may include a microstrip feed line coupled with a gate of a transistor of the switched circuit. The microstrip feed line may be in a direct feed configuration or it may be in an indirect feed configuration.

In some cases, the pulse generator may include a logic gate circuit. For example, the logic gate may include a NAND gate. Optionally, an output of the logic gate may be coupled with a gate of a transistor of the switched circuit.

In some examples, the sensor may also include a processor. The processor may be configured for processing the received reflected ones of the emitted radio frequency pulses to derive an indicator of any one or more of respiration, sleep and heart rate. Optionally, the sensor may also include a respiratory treatment apparatus. The respiratory treatment apparatus may include a flow generator with a processor. The processor of the respiratory treatment apparatus may be configured to process the indicator.

Some embodiments of the present technology may involve a circuit for generating signals to produce radio frequency pulses for range gated physiology sensing. The circuit may include a pulse generator configured to generate signal pulses. These signal pulses can be used to provide the control signals to the switched circuit shown in FIG. 4. The circuit may also include a dielectric resonator oscillator configured to generate a radio frequency oscillating signal. The circuit may also include a switched amplifier circuit coupled to the pulse generator and the dielectric resonator oscillator. The switched amplifier circuit may be configured to generate a pulsed radio frequency oscillating signal in accordance with the signal pulses and radio frequency oscillating signal. The circuit may also include an antenna feed coupled with an output of the switched amplifier circuit to accept the pulsed radio frequency oscillating signal and emit radio frequency pulses in accordance with the pulsed radio frequency oscillating signal via an antenna.

In some cases, the dielectric resonator oscillator may include a dielectric resonator and a transistor. The transistor may have a drain, a gate and a source, and the dielectric resonator may be coupled to the gate and to the drain of the transistor. Optionally, the amplifier may include a transistor having a drain, a gate and a source and the amplifier may be configured to amplify the radio frequency oscillating signal synchronously with the pulse signal to generate the pulsed radio frequency oscillating signal. The drain may be coupled to receive the signal pulses from the pulse generator. The gate may be coupled to receive the radio frequency oscillating signal from the dielectric resonator oscillator.

In some cases, the circuit may also include a filter and a set of magnitude detectors both coupled with the antenna feed. The magnitude detectors may be configured to detect signals received with the antenna feed based on signals generated from the switched amplifier circuit.

Some embodiments of the present technology may involve a circuit for generating signals to produce radio frequency pulses for range gated physiology sensing. The circuit may include a pulse generator configured to generate signal pulses. The circuit may also include a dielectric resonator oscillator configured to generate a radio frequency oscillating signal. The circuit may also include a switched oscillator circuit coupled to the pulse generator and the dielectric oscillator. The switch oscillator circuit may be configured to generate a pulsed radio frequency oscillating signal in accordance with the signal pulses and radio frequency oscillating signal. The circuit may also include an antenna feed coupled with an output of the switched oscillator circuit to accept the pulsed radio frequency oscillating signal and to emit radio frequency pulses in accordance with the pulsed radio frequency oscillating signal via an antenna.

In some cases, the dielectric resonator oscillator may include a dielectric resonator and a transistor. The transistor has a drain, a gate and a source, and the dielectric resonator may be coupled to the gate and to the drain, of the transistor. The switched oscillator circuit may include a wideband oscillator. The wideband oscillator may be configured to injection lock with the dielectric resonator oscillator. Optionally, the switched oscillator circuit may include a transistor having a drain, a gate and a source and the switched oscillator circuit may include a feedback network coupled to the drain. An attenuator and matching network may couple the radio frequency oscillating signal output of the dielectric resonator oscillator with the gate of the transistor of the switched oscillator circuit by a microstrip feed line coupled to the gate of the transistor of the switched oscillation circuit. The microstrip feed line may be in a direct configuration or it may be in an indirect configuration. Optionally, the pulse generator may be coupled with a gate of a transistor of the switched oscillator circuit.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIG. 9 is a signal representation of "dithering" of the pulse generation (in which the underlying pulse repetition frequency is varied linearly).

DETAILED DESCRIPTION

Figure 1:
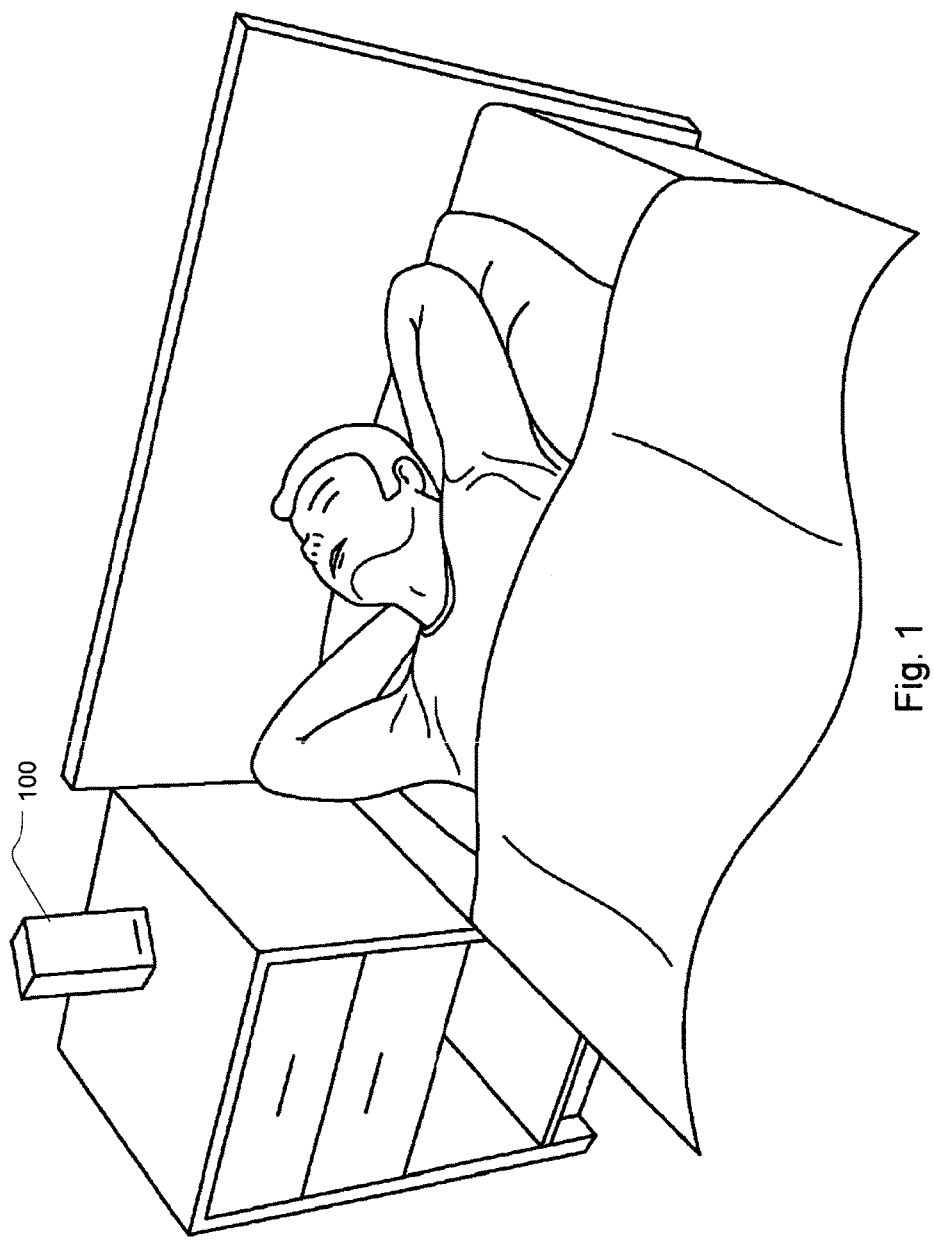
FIG. 1 is an illustration of an example detection apparatus suitable for implementation with a radio frequency physiology sensor of the present technology.

As illustrated in FIG. 1, some embodiments of the present technology may implement a sensing or detection apparatus 100 useful for detecting physiological characteristics of a user or patient in the vicinity of the apparatus. The sensor may be a standalone sensor or may be coupled with other apparatus, such as a respiratory treatment apparatus, so as to provide an automated treatment response based on an analysis of the physiological characteristics detected by the sensor of the apparatus. For example, a respiratory treatment apparatus with a controller and a flow generator may be configured with such a sensor and may be configured to adjust a pressure treatment generated at a patient interface (e.g., mask) in response to physiological characteristics detected by the sensor.

A typical sensor of such an apparatus may employ a transmitter to emit radio frequency waves, such as radio frequency pulses for range gated sensing. A receiver, which may optionally be included in a combined device with the transmitter, may be configured to receive and process reflected versions of the waves. Signal processing may be employed, such as with a processor of the apparatus that activates the sensor, to derive physiological characteristics based on the received reflected signals.

Figure 2:
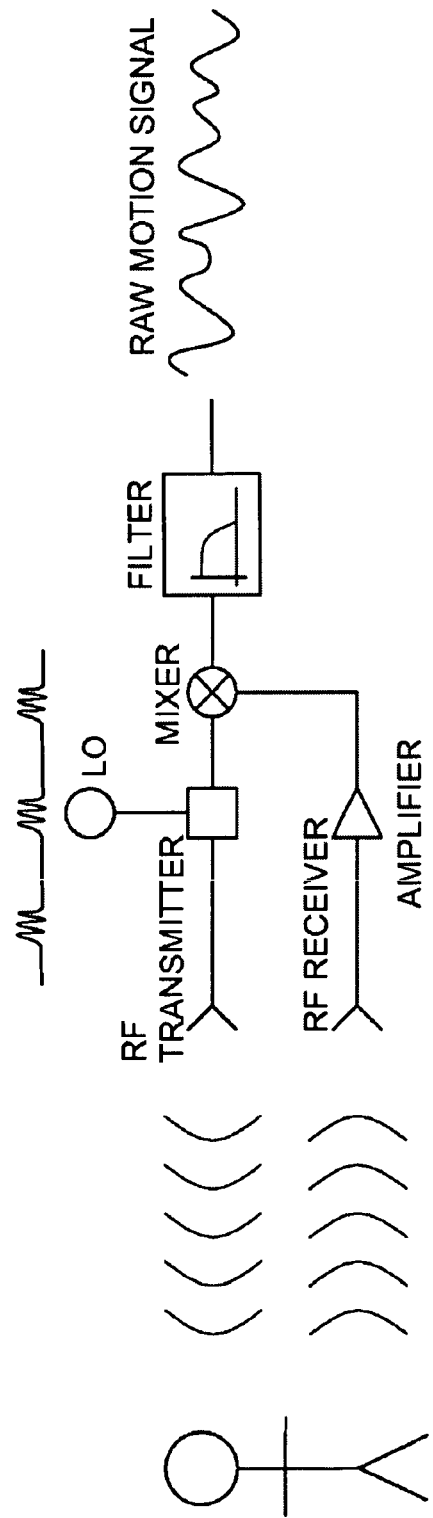
FIG. 2 is a diagram illustrating a conceptual structure and process flow for evaluation of sensor signals suitable for some embodiments of the technology.

For example, as illustrated in FIG. 2, the transmitter transmits a radio-frequency signal towards a subject, e.g., a human. Generally, the source of the RF signal is a local oscillator (LO). The reflected signal is then received, amplified and mixed with a portion of the original signal, and the output of this mixer may then be filtered. The resulting signal may contain information about the movement, respiration and cardiac activity of the person, and is referred to as the raw motion sensor signal.

Figure 3:
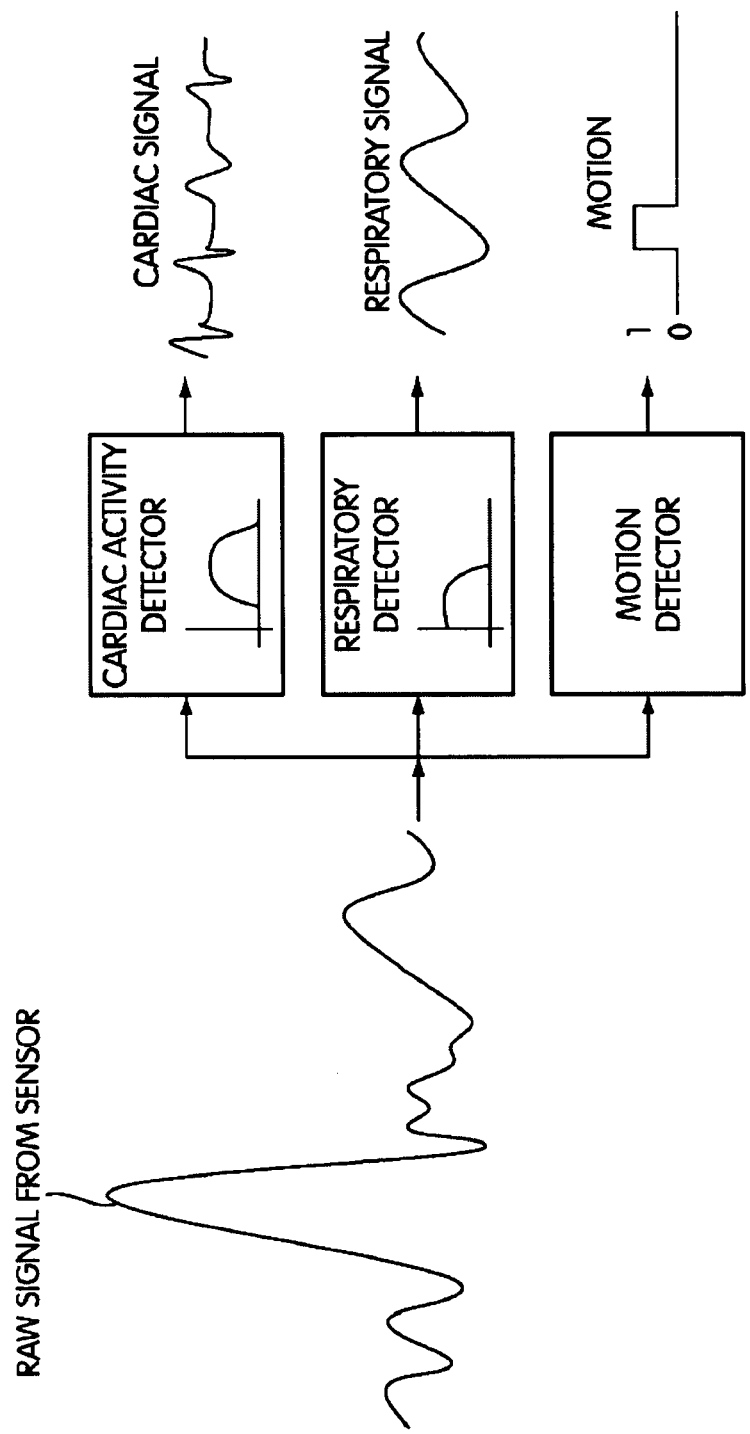
FIG. 3 is a depiction of further processing of sensor signals for the detection of example physiology indicators.

FIG. 3 is a diagram illustrating processing of the raw sensor signal to produce indicators of the physiological characteristics. The raw signal will generally contain components reflecting a combination of bodily movement, respiration, and cardiac activity. Bodily movement can be identified by using zero-crossing or energy envelope detection algorithms (or more complex algorithms), and used to form a "motion on" or "motion off" indicator. For example, such movement detection algorithms may be implemented in accordance with the methodologies disclosed in U.S. Patent Application Publ. No. 2009/0203972, the entire disclosure of which is incorporated herein by reference. The respiratory activity is typically in the range 0.1 to 0.8 Hz, and can be derived by filtering the original signal with a bandpass filter with a passband in that region. The cardiac activity is reflected in signals at higher frequencies, and this activity can be accessed by filtering with a bandpass filter with a pass band of a range from 1 to 10 Hz.

Such a respiration and movement sensor may be a range gated RF motion detector. The sensor may be configured to accept a DC power supply input and provide four analog motion channel outputs with both in-phase and quadrature components of the respiration and movement signals of a person within the detection range. In the case of a pulsed RF motion sensor, range gating can help to limit movement detection to only a preferred zone or range. Thus, detections made with the sensor may be within a defined distance from the sensor.

To achieve range gating in a pulsed RF motion detector system the RF pulses should have a fast turn-on and settling time characteristic. A wideband RF oscillator with a low Q factor tuned circuit may be suitable for such embodiments. Switching the wideband RF oscillator ON and OFF can allow the oscillator to generate the RF pulses. However, wideband oscillators are prone to frequency stability issues. Accordingly, embodiments of the present technology may dramatically improve RF oscillator frequency stability while maintaining the fast switching characteristics required for range gating.

Figure 4:
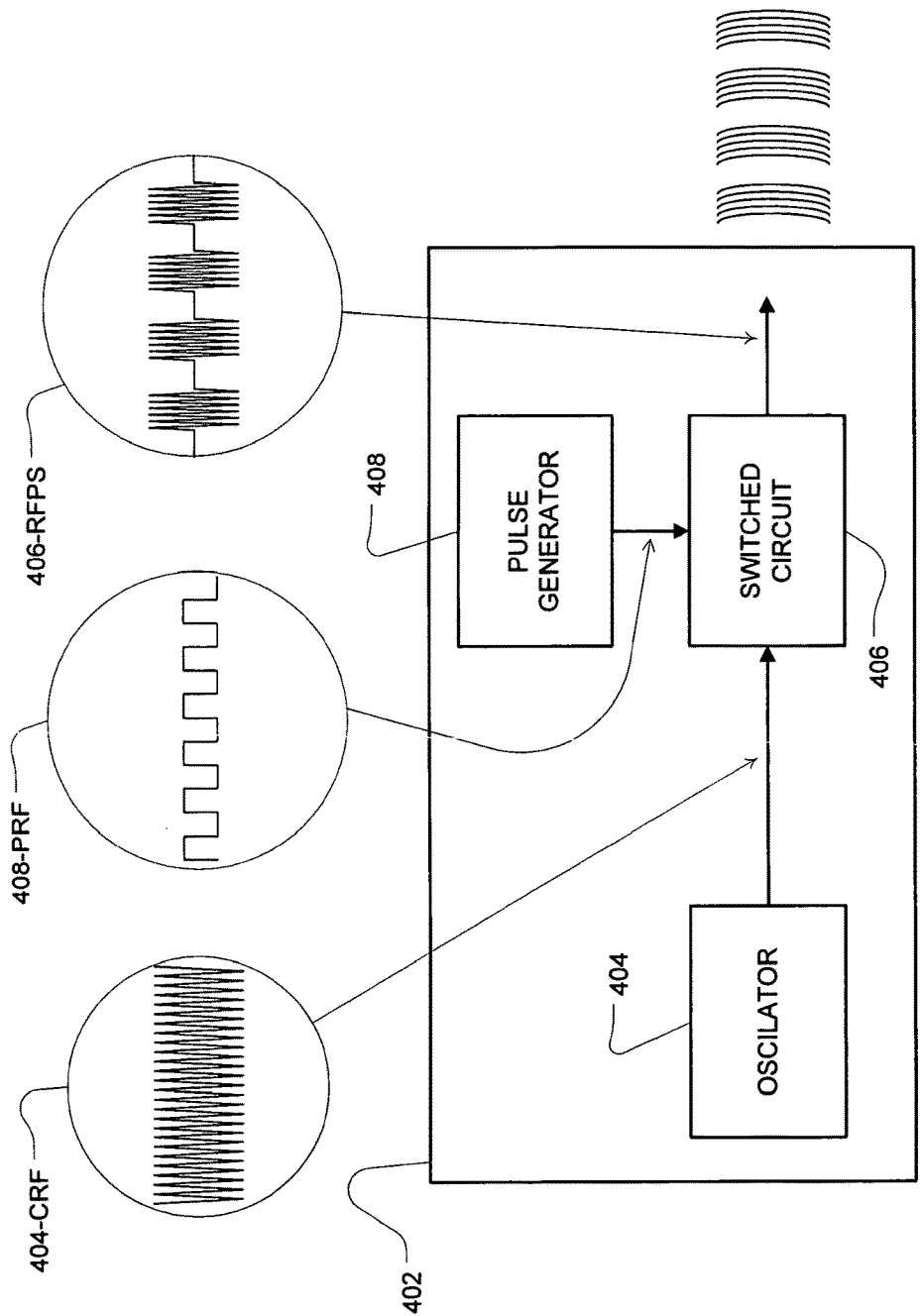
FIG. 4 shows example components involved in a generation of range gated radio frequency signals with switched oscillation in some embodiments of a sensor circuit for the present technology.

For example, as illustrated in FIG. 4, a typical sensor 402 of the present technology may employ an oscillator 404, such as a dielectric resonant oscillator (DRO). The DRO may be a high Q DRO that is a narrowband oscillator (e.g., a DRO operating at 10.525 GHz), such as an oscillator incorporating a puck of dielectric material. The DRO typically generates a stable RF frequency characteristic and is relatively immune to variation in temperature, humidity and component parasitics. However, it may typically have a very slow turn on time and as such cannot be switched ON and OFF fast to provide an RF signal suitable for a range gated system. For example, a typical DRO may switch ON about 1000 times too slowly to meet some sensor range gating requirements.

Accordingly, to address such issues, the oscillator 404 may be coupled with a switched circuit, such as a switched wideband oscillator or a switched amplifier. In such a case, the DRO oscillator 404 may produce a stable RF oscillation signal such as when it is kept continuously ON during pulsed transmissions rather than being powered ON and OFF by switching the DRO oscillator's power source. The stable radio frequency oscillation signal 404-CRF (continuous radio frequency) continuously output from the DRO oscillator 404 may then be applied to an input of the switched circuit 406. Based on a timing pulse signal 408-PRF (pulse repetition frequency) output from a pulse generator 408 to an input of the switched circuit 406, the switched circuit 406 may generate the radio frequency pulse signals 406-RFPS, used for range gating, in synchrony with the pulse signal 408-PRF, to control transmission of the pulsed RF electromagnetic waves from a suitable antenna and antenna feed (not shown in FIG. 4).

In the case of this implementation of the switched circuit, injection locking may be employed to stabilize the switched wideband oscillator to provide both frequency stability and fast oscillator turn on with good OFF attenuation characteristics. Thus, the switched circuit 406, when in the form of a wideband oscillator, may be injection locked by the DRO oscillator 404. In the case of the implementation of the switched circuit 406 using a switched amplifier, the wideband amplification of the DRO oscillator's RF output signal can provide both frequency stability and an even faster turn on time.

Alternatively, in some embodiments, rather than implementing a switched oscillation circuit to generate the pulsed radio frequency signal as illustrated in FIG. 4, one or more semiconductor switches, such as in series, may be implemented to selectively shunt or pass the radio frequency signal. In such alternative embodiments, the switch or switches merely permit selective output of the radio frequency signal due to toggling of the switches. In this sense, the switch, as opposed to the switched oscillation circuit, merely passes the received oscillation signal at certain times. However, there are several disadvantages with such implementations. One such disadvantage of the semiconductor switch architecture is that the components are expensive at microwave frequencies. Another disadvantage with such a switching architecture is that RF signal attenuation (i.e., the ratio of ON signal level to OFF signal level) is low. A high attenuation is required to permit correct range gating performance. Multiple switches, such as in a "T" switch network, can be implemented to mitigate such attenuation issues but may undesirably increase its cost. This embodiment can be considered as a special case of the switched amplifier implementation of FIG. 4 in which the amplifier has a gain of less than or equal to unity.

Figure 5:
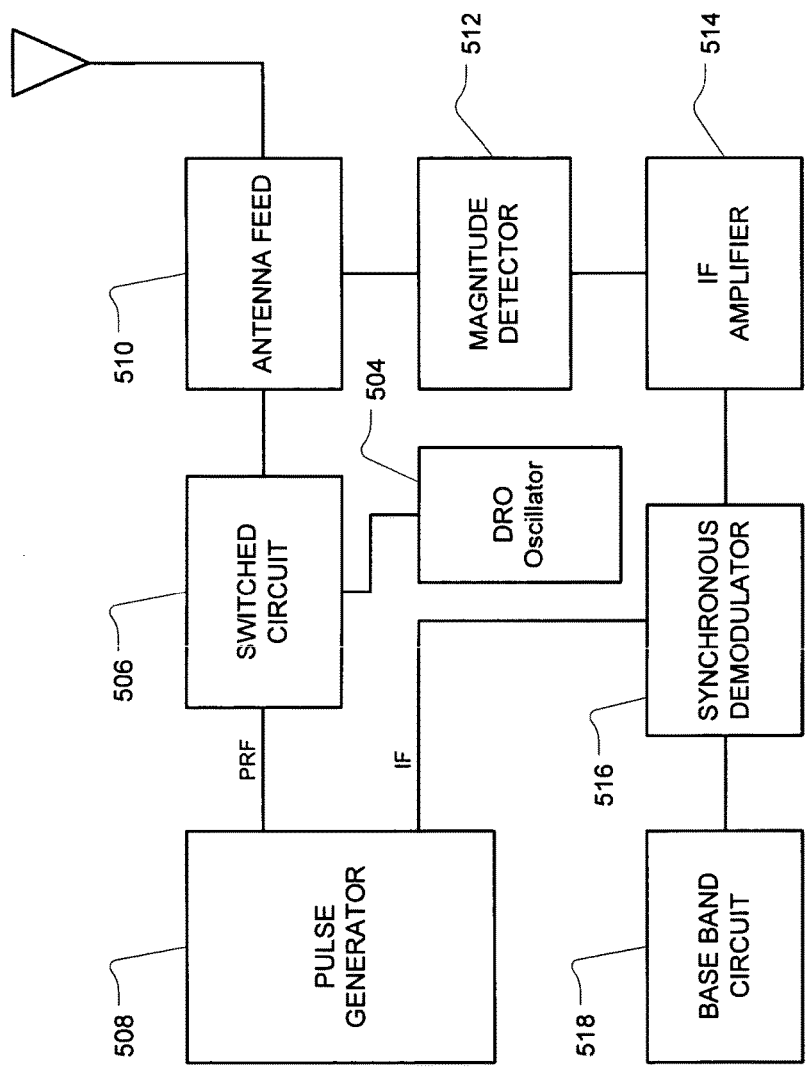
FIG. 5 is an schematic of components for an architecture of an example sensor circuit in some embodiments of the technology.
Figure 5A:
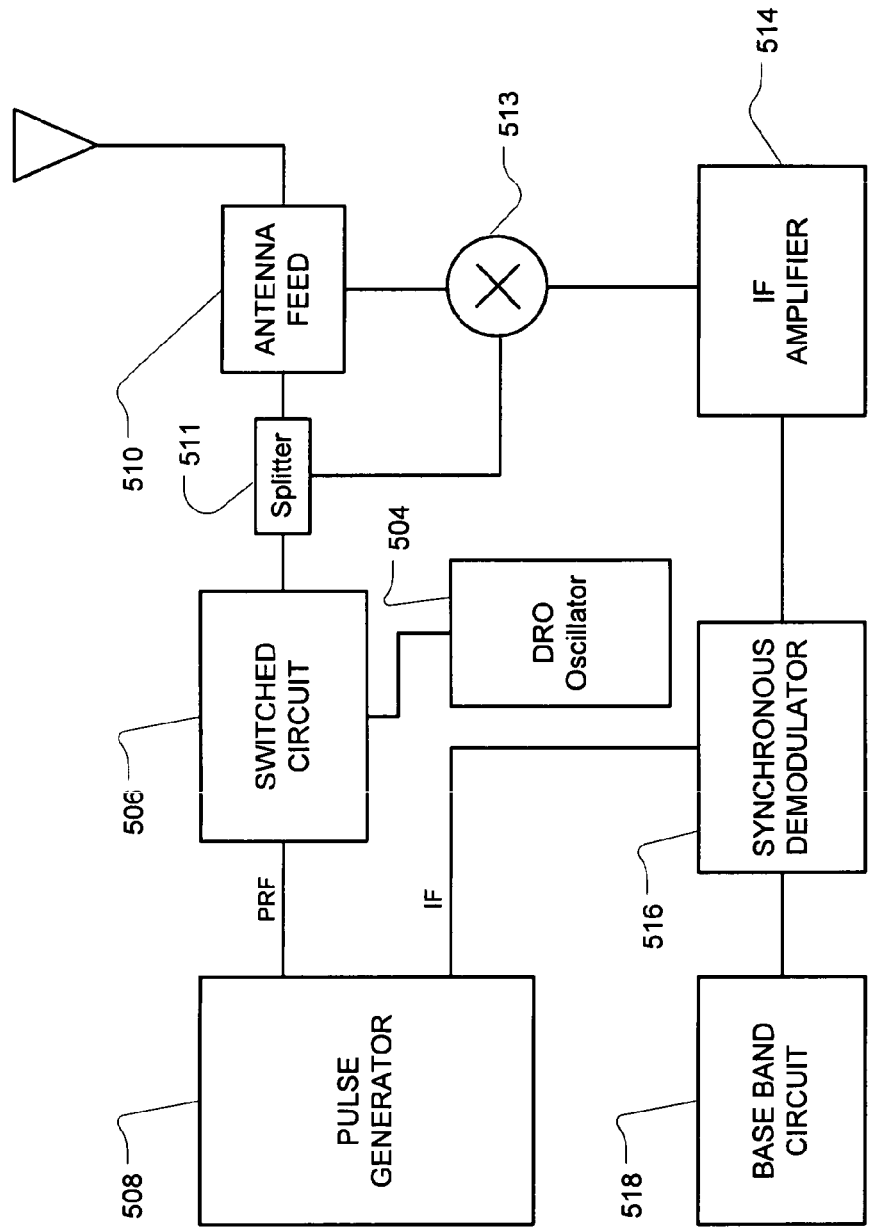
FIG. 5A is an schematic of components for an architecture of another example sensor circuit in some embodiments of the technology.

Example sensor circuit architectures according to some embodiments of the present technology are illustrated in the block diagrams of FIGS. 5 and 5A. The circuit may be a bio-motion sensor implemented as a pulse Doppler radar system operating in, for example, the microwave X-band at a frequency of 10.525 GHz. However, other suitable RF frequencies may be implemented. Some embodiments may optionally employ a method for modulation and demodulation of the pulse radar signal as described in U.S. Pat. No. 6,426,716, the entire disclosure of which is incorporated herein by reference.

As illustrated in FIG. 5, the sensor circuit may be formed by four main sections:

(1) a homodyning transceiver frontend section: This section may include the switched circuit 506, such as a switched 10.525 GHz wideband oscillator or switched amplifier, a DRO oscillator 504, an antenna feed 510 and a magnitude detector 512 for generation and reception of the pulsed RF radar signals;

(2) a pulse generator 508 section: This section may include a digital pulse generator circuit. The generator may be configured to generate the timing pulse signals 508-PRF, 508-IF (IF standing for intermediate frequency) for modulation and demodulation of the RF radar signals;

(3) a dual channel IF amplifier 514 and synchronous IF demodulator 516 for the amplification and demodulation of the received IF signals to produce a baseband signal; and (4) a baseband circuit 518 for the amplification and filtering of the base band signals (e.g., signal processing of the raw signal to derive cardiac, respiratory and/or motion signals).

As shown in the circuit architecture of FIG. 5A, a splitter 511 may optionally be implemented at the output of the switched circuit 506 to route its output signals to a mixer circuit 513 (e.g., multiplier). The mixer circuit 513 may then mix these signals with signals of the reflected and received RF signals as previously discussed herein.

A circuit of the system in some versions may operate according to the following methodology:

(a) The pulse generator circuit 508 generates a PRF timing signal (e.g., 0.5 microsecond duration every 1 microsecond) an example of which is illustrated as signal 408-PRF in FIG. 4). This PRF pulse is used to switch on and off the circuit 506, which is in the form of either an RF wideband oscillator (such as one with a 10.525 GHz oscillation characteristic) or an amplifier. The switched circuit is simultaneously seeded by the signal from the DRO oscillator 504. The output signal of switched circuit 406 is the RF pulse signal illustrated as signal 406-RFPS in FIG. 4. As result, an RF pulse is transmitted via an antenna (e.g., an RF pulse of duration 0.5 microseconds every 1 microsecond). Such an RF pulse train with this characteristic may have a narrow signal bandwidth (e.g., approximately 25 MHz) and may be suitable for range gating applications and/or meeting RF regulatory approval certification.

(b) If the transmitted RF pulse reflects off of a high permittivity target, such as a person, it is reflected back and directed, through the antenna, into the receiver circuit.

(c) Both the transmitted RF signal and received RF signal are presented to the input of a homodyning receiver magnitude detector 512 (e.g., an RF magnitude detector). The homodyning magnitude detector receiver generates a measure of the magnitude and phase of the received signal with respect to the transmitted signal. The phase and/or magnitude of the received signal changes with respect to the transmitted signal when the target moves. As result, the magnitude detector 512 output signal is a measure of the movement of a target. While such a magnitude detector may be optionally implemented, in some cases, other circuit elements or detectors may be implemented in place of or to serve the function of the magnitude detector(s). For example, any detector circuit configured to detect signal amplitude, such as a peak detector, or envelope detector, may be employed.

(d) The homodyning receiver magnitude detector 512 may be switched on (at offset time t0 from the nominal start time of the RF pulse) for a short duration T (e.g., up to 5 nanoseconds) each PRF cycle at the start of the RF pulse, such as in accordance with an output timing signal of the pulse generator 508. (This may be considered an offset time t0). This provides a "t0 Receive Level" that can be used as a reference. This operation is repeated a number of times (N) to obtain an average of the "t0 Receive Level." The duration T determines the approximate width of the ranging zone using the formula "zone=c*T/2" where c is the speed of light. The offset t0 determines the range of the detected zone as objects which are closer than c*(t0)/2 and further than c*(t0+T)/2, will not be detected.

(e) The homodyning magnitude detector receiver may then be switched on for approximately the same duration of time T (e.g., up to 5 nanoseconds each PRF cycle), but at an offset time t1 from the nominal start time of the RF pulse. This may be considered a time "t1". This provides a "t1 Receive Level". This operation may be repeated a number of times (N) to obtain an average of the "t1 Receive Level".

(f) The Intermediate Frequency (IF) is one complete cycle of operation as described above in sections (d) and (e).

Hence, an IF signal generated by the pulse generator may have a frequency of PRF/(2*N).

(g) The difference between the "t0 Receive Level" and the "t1 Receive Level" provides a measure of the movement that has occurred in the time period t1 from the start of the RF pulse and hence the movement that has occurred within the range (c*t1)/2, where c is the speed of the light.

(h) A synchronous demodulator 516 may be implemented to detect the difference between the "t0 Receive Level" and the "t1 Receive Level". As result, it synchronously demodulates the IF modulated receive signal and produces a baseband signal.

(i) The output of the synchronous demodulator is subsequently amplified and filtered by a baseband circuit 518. The circuit may generate separate outputs for respiration and movement since movement and respiration signals are at different frequencies and may be filtered by different filters.

(j) Optionally, to overcome nulls in movement sensitivity that may occur every λ/2 in space, a second "quadrature phase" magnitude detector receiver may be placed at a λ/8 distance from the first "in phase" receiver. For example, in the case of a 10.525 GHz frequency RF signal, the distance λ/8 is 3.55 mm. The physical spacing of this second receive circuit generates a quadrature receiver output which has maximum movement sensitivity at the point of the "in phase" minimum sensitivity.

With such operations, an example pulsed RF range gated motion sensor with a narrow signal bandwidth may be implemented.

Figure 6:
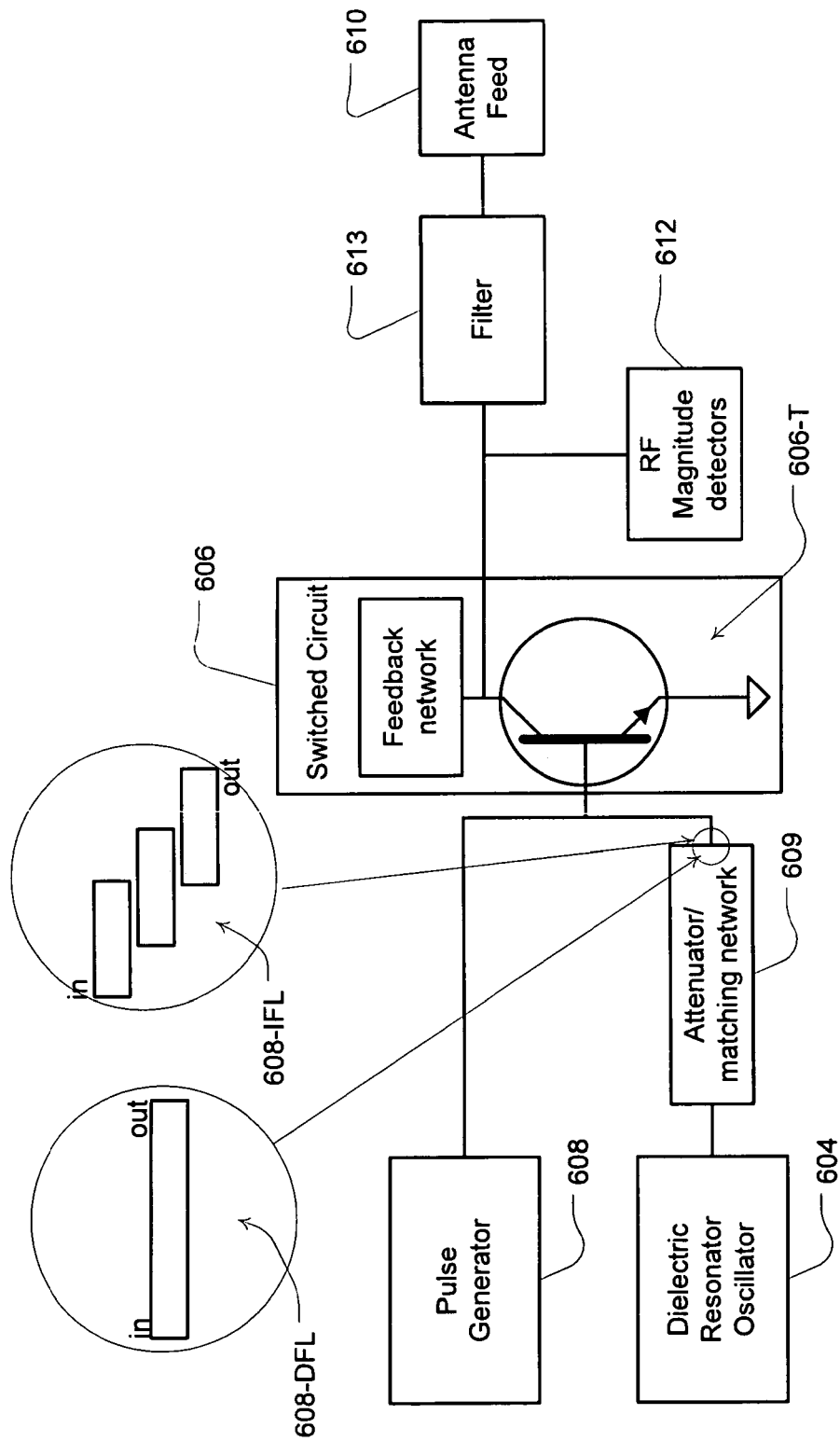
FIG. 6 is a block diagram with example components for an oscillator embodiment of the switched circuit of FIG. 4.

An example embodiment of a frontend section for implementing this range gated pulsed radar system may be considered in reference to the circuit component diagram of FIG. 6. In this embodiment, the switched circuit is implemented as a wideband RF oscillator 606. Typically, a wideband oscillator can be prone to frequency stability issues, such as that caused by humidity and/or temperature variations, component and batch parasitic variations and housing proximity effects. However, the present circuit design permits the oscillator to maintain the RF centre frequency within desired limits (e.g., within approximately 10 MHz of 10.525 GHz). It provides fast switching and a stable pulsed RF signal. It permits a fast turn on of the oscillation circuit while providing a fast stabilisation of frequency and amplitude. The turn on time Δt is related to Q and hence bandwidth (BW) of the oscillator may be as follows:

$$\Delta t = Q/(nf_0) \sim 1/BW.$$

In some cases, the oscillation circuit may optionally be hermetically sealed and/or may optionally include a temperature control circuit.

The oscillator 606 may be injection locked by the DRO oscillator 604. Injection locking occurs when the wideband oscillator 606 is disturbed by the DRO oscillator 604 operating at a nearby frequency. Since the coupling is strong enough and the frequencies near enough, the DRO oscillator can capture the wideband oscillator, causing it to have essentially identical frequency as the DRO oscillator. Thus, in a typical embodiment, these two oscillators have a suitable "lock-in range" for injection locking.

In the circuit variant of FIG. 6, a high stability Dielectric Resonator Oscillator, DRO, circuit 604 may include a transistor (not shown), such as a low noise gallium arsenide (GaAs) Field Effect Transistor (FET) or a Bipolar Junction Transistor (BJT), configured as an amplifier with feedback provided via a frequency stable Dielectric Resonator coupled with microstrip lines to the gate (base) and drain (collector) circuits of this transistor. Such a DRO oscillator, operating at for example, 10.525 GHz, may be implemented for the frequency reference for the radar system centre frequency.

This DRO reference oscillator is configured to maintain the working centre frequency of the sensor within a regulatory specification over the operating temperature and humidity range of the product. This reference oscillator circuit may be enclosed inside a metal cavity to ensure good screening and high quality factor. Also, fine tuning of the centre frequency may optionally be provided by a mechanical tuning screw in a top of a screen above the resonator.

The output signal from the DRO reference oscillator 604 may be fed into the switched wideband oscillator 606 via an attenuator and/or matching network 609 having a feed line to the switched oscillator 606. The attenuator and matching network properties may be configured to ensure that the second oscillator will only oscillate at a frequency determined by the reference oscillator over the working temperature and humidity range of the product. The configuration of the attenuator may set the injection level to the modulated oscillator 606 and hence the capture frequency range. The matching network may be configured to convert the low impedance output of the reference oscillator 604 to higher impedance suitable for injection into the modulated oscillator 606. The matching network may be a shunt-open-circuited-stub: transmission-line: shunt-open-circuited-stub directly coupled network. The feedline from the network 609 may be coupled to the gate (base) of the transistor 606-T. In some embodiments, this microstrip feedline to the transistor may be low-pass, such as when it is formed in a direct feed 608-DFL configuration. However, in some embodiments, the feed line may be high-pass, such as when it is formed in an indirect feed configuration 608-IFL.

The switched oscillator 606 may include a transistor 606-T, such as an FET. This transistor may be configured with a tuned microstrip feedback network, which, in addition to any desired gain characteristics, will include any desired oscillation characteristics suitable for the lock-in range. Some or all of the feedback may be provided by the internal parasitics of the transistor 606-T. This tuned microstrip feedback network may be configured to ensure fast rise and fall time of the output signal required for range gating of the pulse radar system.

The bias circuit of the switched oscillator 606 is also supplied with a digital pulse from the pulse generator 608 so that oscillations can only occur during the application of the switch pulse. As illustrated in FIG. 6, this output of the pulse generator is also input to the gate or base of the transistor 606-T of the switched oscillator 606.

The switched oscillator then produces a frequency radar pulse at the stable reference frequency when a positive pulse is applied to the base circuit by the pulse timing circuit or pulse generator. In some versions, the pulse generator may include a fast logic gate (e.g., a NAND gate or AND gate circuit) to generate the timing pulse. Optionally, the output of the logic gate may be applied to a circuit network configured to maintain a wideband characteristic to ensure fast and effective switching of the switched oscillator.

The pulsed RF frequency output from the switched oscillator 606 is then input to the peak/magnitude detectors 612 and filter(s) 613. Optionally, this pulsed RF frequency output may be input to these components via a series resistor or via an attenuator network. The series resistor can be implemented to optimise the drive level to the magnitude detectors, isolate the switched oscillator from signal reflections and improve system impedance match.

The filter 613 may be implemented with a microstrip bandpass filter and connected to the antenna feed 610. The microstrip bandpass filter may be implemented to ensure high rejection of out of band interfering signals and low harmonic emissions from the sensor. This filter may provide high rejection at radio/TV broadcast, Wi-Fi, DECT, ISM and mobile phone frequencies commonly encountered in domestic and clinical environments. The filter may also provide sufficiently high rejection at the second harmonic frequency (e.g., 21.05 GHz in the case of a 10.525 GHz oscillator) to ensure regulatory product compliance in all world markets. The filter may be a high performance sub-miniature energy-trapping low insertion loss coupled H resonator bandpass filter in some embodiments.

The magnitude detectors 612 can be implemented to provide two phase separated receive I & Q channel IF signals that are proportional to the magnitude sum of the forward propagating and reverse propagating radar signals. In this regard, the inputs to each magnitude detector may be separated along a microstrip feed line by a distance of $\lambda/8$ as previously discussed. However, in any of the embodiments described herein, the separation distance may be different. For example, the I & Q magnitude detector separation distance may be generalized to $+/-(2n-1)\lambda/8$. Thus, the separation distance may optionally be chosen according to any of the following distances: $\lambda/8, 3\lambda/8, 5\lambda/8, 7\lambda/8, \ldots$, etc.

Figure 7:
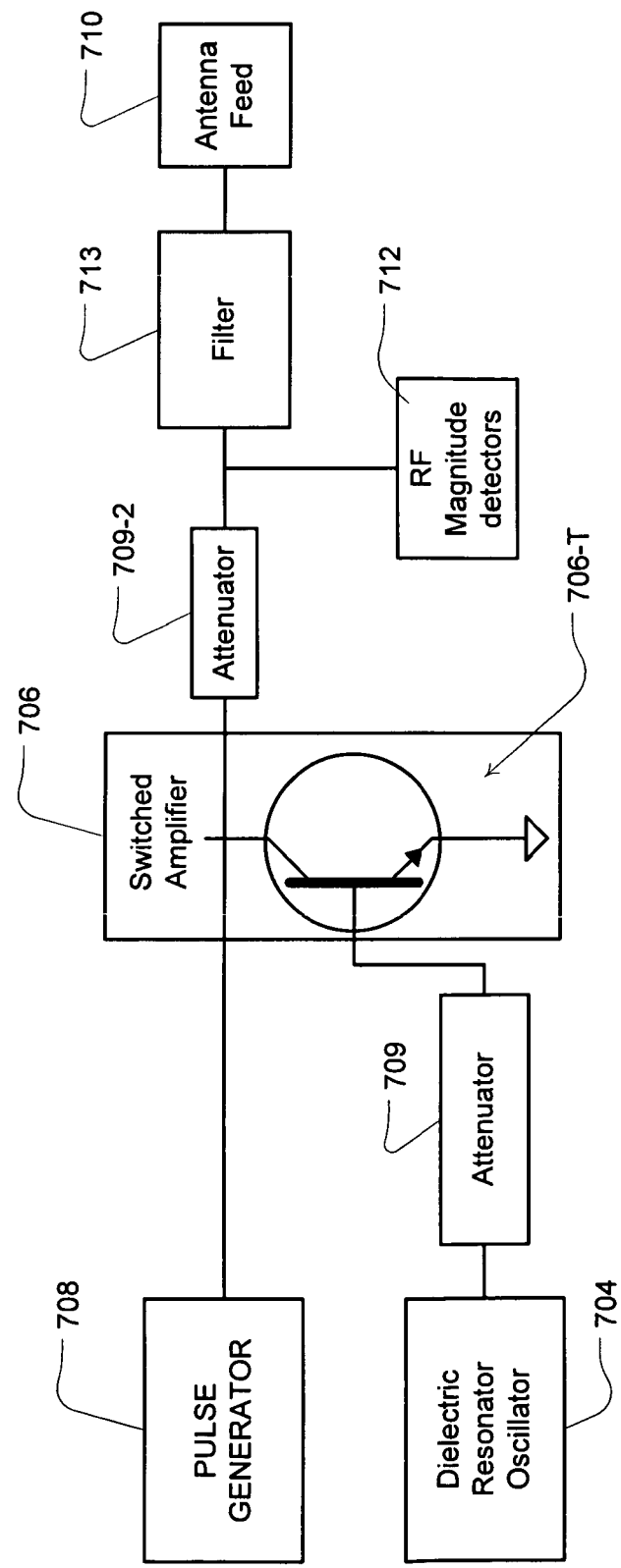
FIG. 7 is a block diagram with example components for an amplifier embodiment of the switched circuit of FIG. 4.
Figure 8:
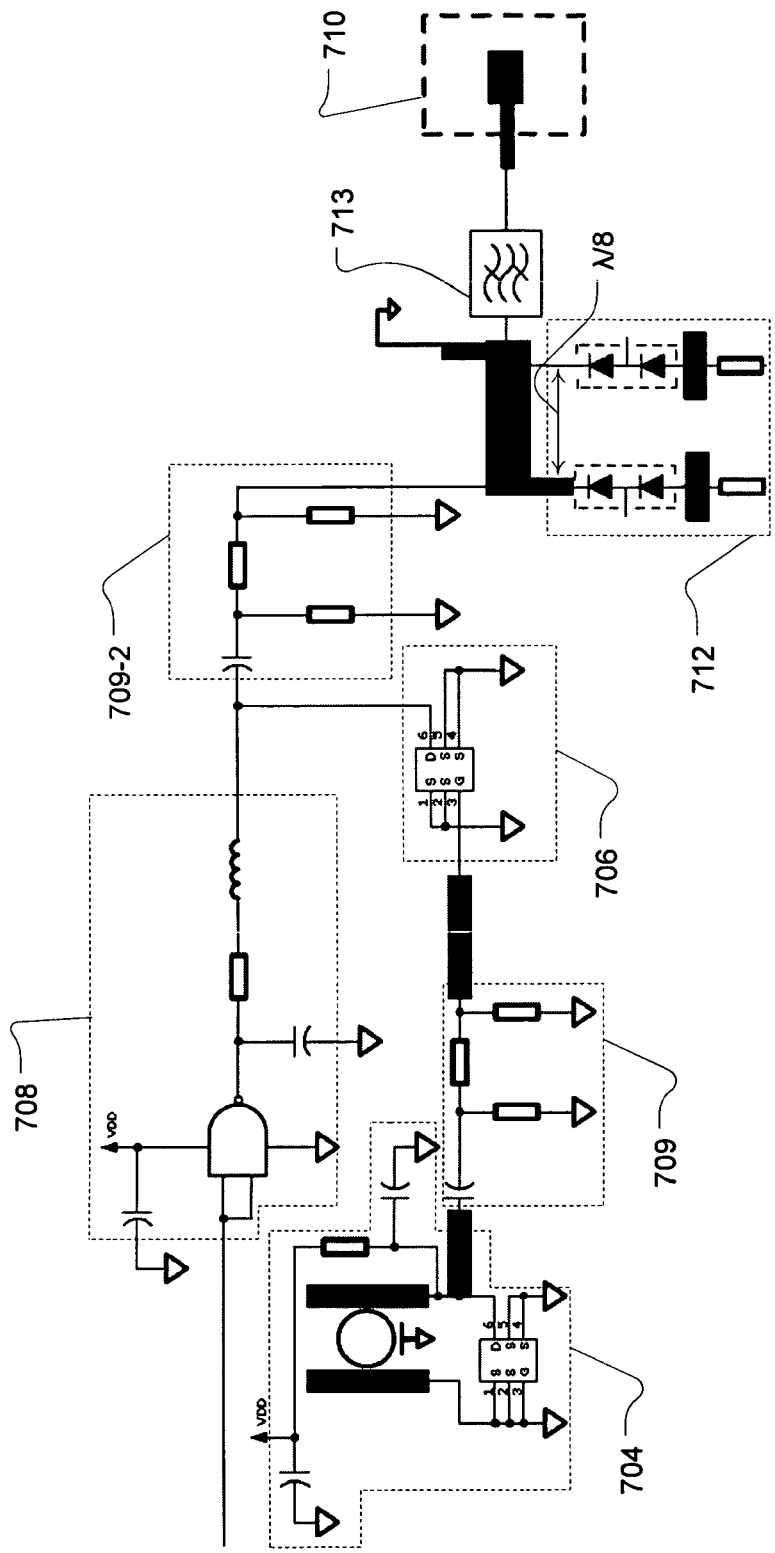
FIG. 8 is a circuit diagram showing an example circuit suitable for implementation as the amplifier embodiment of FIG. 7 in some sensors of the present technology.

Alternative embodiments of the present technology in which the switched circuit is provided in an amplification configuration may be considered in view of the illustrations of FIGS. 7 and 8. This embodiment is similar to that of the embodiment of FIG. 6. However, in this embodiment, rather than having a switched wideband oscillator 606, the circuit employs a switched wideband amplifier 706. In the examples, the amplifier is implemented in a common source configuration. However, alternative configurations may be implemented in some embodiments (e.g., common drain or common gate.)

In this circuit variant, the high stability dielectric resonator oscillator 704 and the pulse generator 708 may employ the configuration discussed with regard to the embodiment of FIG. 6. The output signal from the DRO reference oscillator 704 is input to attenuator 709. The attenuator ensures frequency stable operation of the reference oscillator under all conditions and is configured to apply an optimum drive level to the switched amplifier 706.

The outputs of the attenuator 709 and the pulse generator 708 are coupled to the switched RF power amplifier 706. In this regard, the switched power amplifier may include a transistor 706-T, such as an FET. The pulse switching signal from the pulse generator is applied to the drain (collector) of the transistor 706-T. The attenuated signal from the DRO oscillator 704 is applied to the gate (base) of the transistor 706-T. The source (emitter) of the transistor 706-T may be coupled to a ground, such as a ground plane of a printed circuit board (PCB) on which the circuit is formed.

The switched power amplifier thereby produces an amplified radar pulse at the stable reference frequency (e.g., 10.525 GHz) when a positive pulse is applied to the drain (collector) by the timing of the pulse generator circuit, which may include circuit components, such as series resistor, series inductor and capacitors, configured to ensure fast switching and minimal overshoot of the modulation pulse applied to the modulated amplifier 706.

The pulsed radio frequency output from the modulated power amplifier 706 is fed via an optional second attenuator 709-2, through the magnitude detectors 712, through filter 713 (e.g., bandpass filter as previously described in reference to FIG. 6) to the sensor antenna (such as a horn probe antenna) or antenna feed 710. The second attenuator 709-2 may be configured to optimise the drive level to the magnitude detectors and improve system impedance match. This second attenuator can be omitted in some embodiments.

FIG. 8 is a circuit diagram showing an example circuit suitable for implementation as the amplifier embodiment of FIG. 7 in some sensors of the present technology. Example components thereof have been outlined and numbered accordingly. Some potential advantages of the circuit configuration of FIG. 8 may include the elimination of the lock-in range requirements. As seen in the figure, the circuit complexity associated with implementation of a wideband oscillator is reduced. As a further advantage, the turn on time of the wideband RF amplifier can be faster than the wideband RF oscillator.

In some cases, the timing of the pulse generation circuit can be dithered with respect to the underlying pulse repetition frequency by inclusion of a dithering circuit (not shown) such as one coupled with or included with a pulse generator 408. FIG. 9 shows a signal representation of "dithering" of the pulse generation (in which the onset time of the pulse varies with respect to the overall pulse generation timing). In one embodiment, the overall pulse repetition frequency can be varied, so that the pulse onset time is linearly delayed or advanced with respect to the nominal overall pulse center (i.e., the second pulse train 902 is at a slower pulse repetition frequency than the first pulse train 901). This has the net effect of changing the position of the pulse onset time, compared to its nominal onset time if the PRF remained fixed. This may be achieved with a synchronous ramp dithering circuit. An example synchronous ramp dithering circuit may be implemented with a voltage controlled delay element based on an underlying RC (resistor-capacitor) time constant. The ramp control voltage results in a varying varactor capacitance which in turn results in a varying resonator frequency. In this way the frequency of the pulse generation circuit oscillator and associated PRF is varied on the order of about 1% in a synchronous and linear manner every 1 ms approximately. Dithering is utilised because it removes synchronous RF demodulation noise artefacts. Ramp dithering is utilised because it is easy to realise however it can produce tone artefacts. Synchronous ramp dithering prevents these unwanted tones from being generated.

In this specification, example embodiments are often illustrated with reference to Field Effect Transistors (FETs), in which the three active ports are referred to as the gate, drain and source. However, other circuits may be implemented in its stead. For example, in some cases, alternate technologies such as the Bipolar Junction Transistor (BJT) in which emitter, base and collector are the active elements of the device.

In addition, whilst the main focus of the described technology is associated with applications for detecting respiration, sleep and heart rate, it is similarly suitable for detecting other movements of the human body.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. It will further be understood that any reference herein to subject matter known in the field does not, unless the contrary indication appears, constitute an admission that such subject matter is commonly known by those skilled in the art to which the present technology relates.

In the examples recited herein, certain variables are identified for purposes of explaining the technology herein. In some cases, specific values may be implemented for those variables. For example, N has been illustrated to refer to number of times certain operations may be performed. In some cases, for example, N may be 128. However, a large range may be suitable (e.g., N may be in a range from 16 to 32768) so as to provide plausible designs for different cases. Similarly, t0 and t1 have been referred to an offset time. Such an offset time may, for example, be on the order of nanoseconds, such as 5 ns. Moreover, At has been used to refer to a turn on time. Such a turn on time may also be on the order of nanoseconds, such as for example, 50 ns. In some cases, a "BW" bandwidth of an oscillator described herein, may be on the order of megahertz, such as, for example about 20 MHz.

The invention claimed is:

1. A radio frequency motion sensor comprising:
a radio frequency transmitter, the transmitter configured to emit radio frequency pulses; and
a receiver configured to receive reflected ones of the emitted radio frequency pulses,
the radio frequency transmitter comprising:
a pulse generator configured to generate signal pulses, wherein the pulse generator comprises a logic gate circuit;
a dielectric resonator oscillator configured to generate a stable radio frequency oscillating signal; and
a switched circuit coupled to the pulse generator and the dielectric resonator oscillator, the switched circuit configured to generate a pulsed radio frequency oscillating signal that is modulated by the signal pulses of the pulse generator and whose dominant frequency is derived from the dielectric resonator oscillator.

2. The sensor of claim 1 wherein the dielectric resonator oscillator comprises a dielectric resonator and a transistor.

3. The sensor of claim 1 wherein the switched circuit comprises a switchable radio-frequency amplifier.

4. The sensor of claim 3 wherein the amplifier comprises a transistor having a drain, a gate and a source, the amplifier configured to amplify the radio frequency oscillating signal synchronously with the signal pulses to generate the pulsed radio frequency oscillating signal.

5. The sensor of claim 4 wherein the drain is coupled to receive the signal pulses from the pulse generator.

6. The sensor of claim 4 wherein the gate of the amplifier's transistor is coupled to receive the radio frequency oscillating signal from the dielectric resonator oscillator.

7. The sensor of claim 1 wherein the switched circuit comprises a wideband oscillator, the wideband oscillator configured to injection lock with the dielectric resonator oscillator.

8. The sensor of claim 7 wherein the wideband oscillator comprises a transistor having a drain, a gate and a source, the wideband oscillator including a feedback network circuit coupled to the drain.

9. The sensor of claim 1 further comprising an attenuator and matching network circuit between an output of the dielectric resonator oscillator and an input of the switched circuit.

10. The sensor of claim 9 wherein the matching network circuit comprises a microstrip feed line coupled with a gate of a transistor of the switched circuit.

11. The sensor of claim 10 wherein the microstrip feed line is in a direct feed configuration.

12. The sensor of claim 10 wherein the microstrip feed line is in an indirect feed configuration.

13. The sensor of claim 1 wherein the logic gate circuit comprises a NAND gate.

14. The sensor of claim 1 wherein an output of the logic gate of the logic gate circuit is coupled with a gate of a transistor of the switched circuit.

15. The sensor of claim 1 in which an onset time of the signal pulses is varied with respect to overall signal pulse generation timing.

16. The sensor of claim 1 further comprising a processor, the processor configured for processing the received reflected ones of the emitted radio frequency pulses to derive an indicator of any one or more of body movement, respiration, sleep and heart rate.

17. The sensor of claim 16 further comprising a respiratory treatment apparatus, the respiratory treatment apparatus including a flow generator with a processor, the processor of the respiratory treatment apparatus being configured to process the indicator.

18. The sensor of claim 1 wherein the radio frequency transmitter further comprises a dithering circuit, the dithering circuit coupled with the pulse generator to dither signal pulses generated by the pulse generator.

19. The sensor of claim 18 wherein the dithering circuit comprises a synchronous ramp dithering circuit.

20. A circuit for generating signals to produce radio frequency pulses for range gated physiology sensing, the circuit comprising:
a pulse generator configured to generate signal pulses, wherein the pulse generator comprises a logic gate circuit;
a dielectric resonator oscillator configured to generate a radio frequency oscillating signal;
a switched amplifier circuit coupled to the pulse generator and the dielectric resonator oscillator, the switched amplifier circuit configured to generate a pulsed radio frequency oscillating signal in accordance with the signal pulses and radio frequency oscillating signal;
an antenna feed coupled with an output of the switched amplifier circuit to accept the generated pulsed radio frequency oscillating signal and emit radio frequency pulses in accordance with the pulsed radio frequency oscillating signal via an antenna; and
a dithering circuit coupled with the pulse generator to dither the signal pulses generated by the pulse generator.

21. The circuit of claim 20 wherein the dithering circuit comprises a synchronous ramp dithering circuit.

22. A circuit for generating signals to produce radio frequency pulses for range gated physiology sensing, the circuit comprising:

a pulse generator configured to generate signal pulses, wherein the pulse generator comprises a logic gate circuit;

a dielectric resonator oscillator configured to generate a radio frequency oscillating signal;

a switched circuit coupled to the pulse generator and the dielectric resonator oscillator, the switched circuit configured to generate a pulsed radio frequency oscillating signal in accordance with the signal pulses and radio frequency oscillating signal; and an antenna feed coupled with an output of the switched circuit to accept the pulsed radio frequency oscillating signal and to emit radio frequency pulses in accordance with the pulsed radio frequency oscillating signal via an antenna.

23. The circuit of claim 22 wherein the dielectric resonator oscillator comprises a dielectric resonator and a transistor.

24. The circuit of claim 23 wherein the transistor has a drain, a gate and a source, and wherein the dielectric resonator oscillator is coupled to the gate and to the drain of the transistor.

25. The circuit of claim 22 wherein the switched circuit comprises a switched wideband oscillator, the wideband oscillator configured to injection lock with the dielectric resonator oscillator.

26. The circuit of claim 22 wherein the switched circuit comprises a transistor having a drain, a gate and a source, the switched circuit including a feedback network coupled to the drain.

27. The circuit of claim 26 wherein an attenuator and matching network couples the radio frequency oscillating signal output of the dielectric resonator oscillator with the gate of the transistor of the switched circuit by a microstrip feed line coupled to the gate of the transistor of the switched circuit.

28. The circuit of claim 27 wherein the microstrip feed line is in a direct configuration.

29. The circuit of claim 27 wherein the microstrip feed line is in an indirect configuration.

30. The circuit of claim 22 wherein the pulse generator is coupled with a gate of a transistor of the switched circuit.

31. The circuit of claim 22 further comprising a dithering circuit, the dithering circuit coupled with the pulse generator to dither signal pulses generated by the pulse generator.

32. The circuit of claim 31 wherein the dithering circuit comprises a synchronous ramp dithering circuit.

* * * * *